United States Patent [19]

Desmurs et al.

[11] Patent Number: 4,827,047

[45] Date of Patent: May 2, 1989

[54] CHLORINATION OF NITROPHENOLS

[75] Inventors: Jean-Roger Desmurs, Saint-Symphorien D'Ozon; Isabelle Jouve, Villeurbanne, both of France

[73] Assignee: Rhone-Poulenc Chimie, Courbevoie, France

[21] Appl. No.: 164,894

[22] Filed: Mar. 7, 1988

[30] Foreign Application Priority Data

Mar. 5, 1987 [FR]   France ................................ 87 03209

[51] Int. Cl.$^4$ .............................................. C07C 79/32
[52] U.S. Cl. ..................................... 568/709; 568/706; 568/779
[58] Field of Search ................ 568/709, 706, 774, 779

[56] References Cited

U.S. PATENT DOCUMENTS 2,629,745  2/1953  Gilbert et al. ........................ 568/709
2,659,759  11/1953  Zemba .................................. 568/779

FOREIGN PATENT DOCUMENTS

| 216714 | 4/1987 | European Pat. Off. | 568/776 |
| 2212333 | 9/1987 | Japan | 568/776 |
| 2258332 | 11/1987 | Japan | 568/776 |
| 639054 | 10/1983 | Switzerland | 568/776 |
| 2044246 | 10/1980 | United Kingdom | 568/776 |

*Primary Examiner*—Werren B. Lone
*Attorney, Agent, or Firm*—Burns, Doane, Swecker & Mathis

[57] ABSTRACT

The chloronitrophenols, e.g., 2,6-dichloro-4-nitrophenol (a known agrochemical/pharmaceutical intermediate), are efficiently prepared by chlorinating ortho- or para-nitrophenol with gaseous chlorine, characteristically in the molten state, and in the presence of a catalytically effective amount of a primary, secondary or tertiary amine.

14 Claims, No Drawings

CHLORINATION OF NITROPHENOLS

CROSS-REFERENCE TO COMPANION APPLICATIONS

Copending applications, Ser. Nos. 165,007 and 164,966 both filed concurrently herewith and both assigned to the assignee hereof.

BACKGROUND OF THE INVENTION

1. Field of the Invention

The present invention relates to the chlorination of nitrophenols and, more especially, to the chlorination of nitrophenols using gaseous chlorine.

2. Description of the Prior Art

The chloronitrophenols are known compounds, and 2,6-dichloro-4-nitrophenol, for example, is a valuable chemical intermediate, useful in agrochemistry, after hydrogenation to 4-amino-2,6-dichlorophenol, or as a pharmaceutical intermediate after methylation of the phenol group.

2,4-Dichloro-6-nitrophenol can be used, in particular, as an enzyme inhibitor.

The monochloronitrophenols can be used as fungicides, or as intermediates for the preparation of other fungicides.

The chlorination of a nitrophenol is, however, difficult, since the presence of the $NO_2$ group on the benzene ring strongly deactivates the molecule.

SUMMARY OF THE INVENTION

Accordingly, a major object of the present invention is the provision of an improved process for the chlorination of nitrophenols to monochloronitrophenols or dichloronitrophenols by conducting the reaction in the presence of an amine.

Briefly, the present invention features the chlorination of ortho-nitrophenol or para-nitrophenol with gaseous chlorine, wherein the reaction is carried out in the molten state and in the presence of a catalytically effective amount of a primary, secondary or tertiary amine.

DETAILED DESCRIPTION OF THE PREFERRED EMBODIMENTS OF THE INVENTION

More particularly according to the present invention, by the term "amine" is intended any organic nitrogen compound that is liquid or solid under the working conditions of the subject process and contains one or more amine groups.

Such a compound can also contain one or more other functional groups such as, for example, the hydroxyl group, the carboxylic acid group, the carboxylic acid ester group, the amide group or the imine group.

It will of course be appreciated that the amines can also be introduced in the form of their salts, and more especially their respective hydrochlorides.

In the present text, by the term "amine" is also intended ammonia, as well as the salts and, in particular, the amine hydrochlorides.

The amines which serve as a catalyst in the subject process are more preferably the amines having the general formula (I):

in which $R_1$, $R_2$ and $R_3$, which may be identical or different, are each a linear alkyl radical having from 1 to 12 carbon atoms, secondary alkyl radical having from 3 to 12 carbon atoms or a tertiary alkyl radical having from 4 to 12 carbon atoms, with the proviso that such alkyl radicals may contain one or two —O— ether groups or hydroxyl, amine, carboxylic acid, carboxylic acid ester, amide or imine groups; a phenyl radical, a cyclohexyl radical, a cycloheptyl radical or a cyclopentyl radical; a phenylalkyl, cyclohexylalkyl, cycloheptylalkyl or cyclopentylalkyl radical, the alkyl moiety of which contains from 1 to 4 carbon atoms; or a hydrogen atom; with the further provisos that:

$R_1$ may be an $NH_2$ group;

$R_2$ and $R_3$ may from, together with the nitrogen atom from which they depend a saturated heterocycle or a heterocycle containing one or more double bonds, optionally substituted with one or more alkyl groups having from 1 to 4 carbon atoms;

$R_2$ and $R_3$ or $R_1$, $R_2$ and $R_3$ may form, together with the nitrogen atom from which they depend and with one or more other nitrogen and/or oxygen and/or sulfur atoms, a saturated or unsaturated heterocycle optionally substituted with one or more alkyl groups having from 1 to 4 carbon atoms;

$R_1$, $R_2$ and $R_3$ may form, together and with the nitrogen atom from which they depend, an unsaturate heterocycle optionally substituted with one or two methyl or ethyl groups;

$R_2$ and $R_3$ or $R_1$, $R_2$ and $R_3$ may form, together with the nitrogen atom from which they depend and optionally with one or more other nitrogen and/or oxygen and/or sulfur atoms, a saturated or unsaturated polycyclic compound optionally substituted with one or more alkyl groups having 1 to 4 carbon atoms.

Exemplary of such amines of formula (I), the following are representative:

(i) ammonia;

(ii) primary amines such as n-propylamine, isopropylamine, isobutylamine, n-butylamine, tertbutylamine, n-pentylamine, 2-methylbutylamine, 3-methylbutylamine, n-hexylamine, 2-ethylhexylamine, aniline, laurylamine, cyclohexylamine, cyclopentylamine, benzylamine, guanidine, acetamidine, glycine ether ester, ethanolamine, ethylenediamine, hexamethylenediamine, N-aminoethylpyrrolidine, pyrazoline, lysine, n-aminomorpholine and N-aminopiperidine;

(iii) secondary amines such as dibutylamine, dipropylamine, methylpropylamine, methylbutylamine, methylisobutylamine, methyl-tert-butylamine, methylbenzylamine, di-tert-butylamine, 1-methylcyclopentylamine, 1-methylcyclohexylamine, dicyclohexylamine, morpholine, imidazole, pyrrolidine, imidazolidine, piperazine and indole;

(iv) tertiary amines such as triethylamine, tributylamine, pyridine, tris(3,6-dioxaheptyl) amine and 1,8-diazabicyclo[5.4.0]undec-7-ene.

It is also possible to use amino compounds such as hydrazine or its derivatives, in particular the derivatives obtained by substitution of one or two hydrogen atoms with alkyl, aryl, cycloaliphatic or heterocyclic radicals.

The quantity of the amine used in the process can vary over very wide limits.

It usually represents from 0.005% to 10% by weight relative to the weight of the nitrophenol. Preferably, from 0.015% to 5% by weight of amine relative to the nitrophenol will be employed, in order to have sufficient efficacy, while not having an excessive amount of the amine.

Among the amines of the general formula (I), more preferred are the primary or secondary amines of the formula (II):

in which $R_2$ or $R_3$ may be a hydrogen atom; and $R_2$ and $R_3$, which may be identical or different, are each a linear alkyl radical having from 1 to 10 carbon atoms; a secondary alkyl radical having from 3 to 10 carbon atoms; a tertiary alkyl radical having from 4 to 10 carbon atoms; a cyclohexyl or cyclopentyl radical; a phenyl radical; or a benzyl or phenethyl radical; with the provisos that:

$R_2$ and $R_3$ may form, together with the nitrogen atom from which they depend and with another nitrogen and/or oxygen atom, a saturated heterocycle or a heterocycle containing one or more unsaturated bonds; and $R_2$ and/or $R_3$ may contain one or more amine, hydroxyl or carboxylic acid ester groups.

As specific examples of primary amines of the general formula (II), representative are n-propylamine, isopropylamine, n-butylamine, isobutylamine, tertbutylamine, n-pentylamine, 2-methylpentylamine, 3-methylpentylamine, 2-ethylhexylamine, laurylamine, cyclohexylamine, cyclopentylamine, benzylamine, glycine ethyl ester and ethanolamine.

As regards, more especially, the secondary amines of general formula (II), more preferred are those in which at least one of the symbols $R_2$ and $R_3$, and preferably both symbols $R_2$ and $R_3$, are a secondary alkyl radical having from 3 to 10 carbon atoms, such as isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonyl, 3-nonyl, 4-nonyl, 5-nonyl, 2-decyl, 3-decyl, 4-decyl and 5-decyl; a cyclohexyl or cyclopentyl radical; and those in which $R_2$ and $R_3$ form, together with the nitrogen atom from which they depend, a heterocycle optionally containing another nitrogen atom or an oxygen atom.

As specific examples of such secondary amines, diisopropylamine, diisobutylamine, dicyclohexylamine, morpholine and imidazole are representative.

The amine catalysis of the chlorination of nitrophenols permits an improved binding of the chlorine to the nitrophenol molecule, and more especially promotes binding of the second chlorine atom.

On the other hand, without the amine, it is necessary to have a large excess of chlorine beginning at the stage of the first chlorination; this excess is much smaller in the presence of amine.

The amount of chlorine used in the present invention depends principally on the stage of chlorination desired.

If it is desired to stop the chlorination at the monochloronitrophenol stage, it is not necessary to have a mole ratio chlorine introduced/nitrophenol charged very much greater than the stoichiometric proportion. In general, this mole ratio will range from 1 to 2.

If it is desired to form dichloronitrophenol, it is preferable to have a mole ratio chlorine introduced/nitrophenol charged of from 2 to 10, and more preferably from 3 to 6.

In practice, the chlorine is typically introduced by bubbling same into the reaction medium. The pressure in the apparatus is hence substantially equal to or slightly greater than atmospheric pressure.

The chlorine can be used alone or can be diluted with an inert gas such as nitrogen, for example. The presence of an inert gas enables, if necessary, the gaseous flow rate to be increased without a concomitant increase in the amount of chlorine introduced over a given time period.

The gaseous chlorine used in the present process can also be formed in situ, from hydrochloric acid, by adding an oxidizing compound such as, for example, hydrogen peroxide.

Another very attractive advantage of the chlorination of nitrophenols in the presence of an amine is in the modification of the selectivity of the reaction.

In effect, when ortho-nitrophenol is chlorinated without an amine, a large preponderance of 4-chloro-2-nitrophenol relative to 2-chloro-6-nitrophenol is formed in the first stage of the chlorination.

When the reaction is carried out in the presence of an amine, 2-chloro-6-nitrophenol becomes preponderant. Thus, a selective process for producing 2-chloro-6nitrophenol from ortho-nitrophenol is realized.

The temperature at which the process of the invention is carried out is generally below or equal to 200° C. The lower limit is not critical. It is dependent on the need for a liquid reaction mixture.

The preferred temperatures will be between the melting point of the nitrophenol introduced and 150° C.

The process of the invention may be carried out in continuous or discontinuous fashion.

In order to further illustrate the present invention and the advantages thereof, the following specific examples are given, it being understood that same are intended only as illustrative and in nowise limitative.

EXAMPLE 1

A 250-cm³ glass round-bottomed flask equipped with a mechanical stirrer, a dipping tube for the injection of chlorine, a reflux condenser and thermometer pocket was charged with:

(i) para-nitrophenol: 34.78 g (0.250 mol);

(ii) diisopropylamine: 0.34 g (1% by weight relative to the para-nitrophenol).

The mixture was heated under stirring at 120° C. using a thermostatic bath, and gaseous chlorine was then introduced via the dipping tube at a flow rate of 5 1/hr. The temperature was maintained at 120° C. throughout the chlorination.

After 2 hr, 15 min. of chlorination, which represented the introduction of 0.5 mol of chlorine, the composition of the final reaction mixture was analyzed by high performance liquid chromatography (HPLC), The following results were obtained:

(1) degree of conversion (DC) of para-nitrophenol: 100%

(2) yield (YLD) of 2-chloro-4-nitrophenol: 76.3%

(3) YLD of 2,6-dichloro-4-nitrophenol: 23.7%

COMPARATIVE EXPERIMENT A

Example 1 was repeated under the same conditions, but without the inclusion of an amine. The following results were obtained:
(1) degree of conversion (DC) of para-nitrophenol: 98.8%
(2) yield (YLD) of 2-chloro-4-nitrophenol: 86.2%
(3) YLD of 2,6-dichloro-4-nitrophenol: 13.8%

EXAMPLE 2 AND COMPARATIVE EXPERIMENT B

The apparatus described in Example 1 was charged with:
(i) ortho-nitrophenol (ONP): 34.78 g (0.250 mol);
(ii) diisopropylamine: 0.34 g (1% by weight relative to the orthonitrophenol).

The mixture was heated under stirring to 75° C., and gaseous chlorine was then introduced at a flow rate of 5 l/hr.

The temperature was maintained at 75° C. throughout the chlorination.

After 1 hr, 07 min. of chlorination, which represented the introduction of 0.25 mol of chlorine, a sample of the reaction mixture was withdrawn and analyzed by HPLC and by nuclear magnetic resonance (NMR).

The chlorination was continued. After 2 hr, 15 min. which represented the introduction of 0.50 mol of chlorine, the experiment was stopped and the final mixture analyzed by HPLC and NMR.

The same experiment was repeated under the same conditions, but without an amine.

The Table below reports the results obtained for Example 2 and Experiment B, at each of the two stages of chlorination.

TABLE

|  | EXAMPLE 2 | COMPARATIVE EXPERIMENT B |
|---|---|---|
| FIRST STAGE OF CHLORINATION | | |
| DC of orthonitrophenol | 78% | 41% |
| YLD of 2-chloro-6-nitrophenol | 66% | 10% |
| YLD of 4-chloro-2-nitrophenol | 29% | 90% |
| Ratio ortho deriv./para deriv.* | 2.3 | 0.11 |
| YLD of 2,4-dichloro-6-nitrophenol | 5% | 0% |
| SECOND STAGE OF CHLORINATION | | |
| DC of orthonitrophenol | 100% | 88% |
| YLD of 2-chloro-6-nitrophenol | 49% | 14% |
| YLD of 4-chloro-2-nitrophenol | 21% | 84% |
| Ratio ortho deriv./para deriv.* | 2.3 | 0.17 |
| YLD of 2,4-dichloro-6-nitrophenol | 30% | 2% |

*Mole ratio 2-chloro-6-nitrophenol (ortho derivative)/4-chloro-2-nitrophenol (para derivative).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a chloronitrophenol, comprising reacting ortho- or para-nitrophenol with gaseous chlorine in the presence of a catalytically effective amount of a primary, secondary or tertiary amine.

2. The process as defined by claim 1, comprising carrying out the reaction in the molten state.

3. The process as defined by claim 2, said amine catalyst having the general formula (I):

in which $R_1$, $R_2$ and $R_3$, which may be identical or different, are each a linear alkyl radical having from 1 to 12 carbon atoms, a secondary alkyl radical having from 3 to 12 carbon atoms or a tertiary alkyl radical having from 4 to 12 carbon atoms, with the proviso that such alkyl radicals may contain one or two —O— ester groups or hydroxyl, amine, carboxylic acid, carboxylic acid ester, amide or imine groups; a phenyl radical, a cyclohexyl radical, a cycloheptyl radical or a cyclopentyl radical; a phenylalkyl, cyclohexylalkyl, cycloheptlalkyl or cyclopentylalkyl radical, the alkyl moiety of which contains from 1 to 4 carbon atoms; or a hydrogen atom; with the further provisos that:

$R_1$ may be an $NH_2$ group;

$R_2$ and $R_3$ may form, together with the nitrogen atom from which they depend, a saturated heterocycle or a heterocycle containing one or more double bonds, or a saturated heterocycle or a heterocycle containing one or more double bonds substituted with one or more alkyl groups having from 1 to 4 carbon atoms;

$R_2$ and $R_3$ or $R_1$, $R_2$ and $R_3$ may form, together with the nitrogen atom from which they depend and with one or more other nitrogen or oxygen or sulfur atoms or combinations thereof, a saturated or unsaturated heterocycle or a saturated or unsaturated heterocycle substituted with one or more alkyl groups having from 1 to 4 carbon atoms;

$R_1$, $R_2$ and $R_3$ may form, together and with the nitrogen atom from which they depend, an unsaturated heterocycle or an unsaturated heterocycle substituted with one or two methyl or ethyl groups; and $R_2$ and $R_3$ or $R_1$, $R_2$ and $R_3$ may form, together with the nitrogen atom from which they depend or together with the nitrogen atom from which they depend with one or more nitrogen or oxygen or sulfur atoms or combinations thereof, a saturated or unsaturated polycyclic compound or a saturated or unsaturated polycylic compound substituted with one or more alkyl groups having 1 to 4 carbon atoms.

4. The process as defined by claim 3, wherein the amount of said amine present constitutes from 0.005% to 10% by weight of the nitrophenol.

5. The process as defined by claim 2, said amine catalyst having the general formula (II):

in which $R_2$ or $R_3$ may be a hydrogen atom; and $R_2$ and $R_3$, which may be identical or different, are each a linear alkyl radical having from 1 to 10 carbon atoms; a secondary alkyl radical having from 3 to 10 carbon atoms; a tertiary alkyl radical having from 4 to 10 carbon atoms; a cyclohexyl or cyclopentyl radical; a phenyl radical; or a benzyl or phenethyl radical; with the provisos that:

$R_2$ and $R_3$ may form, together with the nitrogen atom from which they depend and with another nitrogen atom or oxygen atom or both a nitrogen atom and an oxygen atom, a saturated heterocycle or a heterocycle containing one or more olefinic double bonds; and $R_2$ or $R_3$ or both $R_2$ and $R_3$ may contain one or more amine, hydroxyl or carboxylic acid ester groups.

6. The process as defined by claim 5, wherein said amine catalyst having the general formula (II), at least one of $R_2$ and $R_3$ is a secondary alkyl radical having from 3 to 10 carbon atoms.

7. The process as defined by claim 6, wherein at least one of $R_2$ and $R_3$ is an isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonyl, 3-nonyl, 4-nonyl, 5-nonyl, 2-decyl, 3-decyl, 4-decyl, 5-decyl, cyclohexyl or cyclopentyl radical.

8. The process as defined by claim 5, wherein said amine catalyst having the general formula (II), $R_2$ and $R_3$ together form, with the nitrogen atom from which they depend, a 5- or 6-membered heterocycle or a 5- or 6-membered heterocycle containing another nitrogen atom or an oxygen atom.

9. The process as defined by claim 5, wherein said amine catalyst having the general formula (II) comprises n-propylamine, isopropylamine, n-butylamine, isobutylamine, tert-butylamine, n-pentylamine, 2-methylpentylamine, 3-methylpentylamine, 2-ethylhexylamine, laurylamine, cyclohexylamine, cyclopentylamine, benzylamine, glycine ethyl ester, ethanolamine, diisopropylamine, diisobutylamine, dicyclohexylamine, morpholine or imidazole.

10. The process as defined by claim 2, carried out at a temperature ranging from the melting point of the nitrophenol to 150° C.

11. The process as defined by claim 2, wherein the mole ratio gaseous chlorine/nitrophenol ranges from 1 to 2.

12. The process as defined by claim 2, wherein the mole ratio gaseous chlorine/nitrophenol ranges from 2 to 10.

13. The process as defined by claim 12, said ratio ranging from 3 to 6.

14. The process as defined by claim 2, wherein 2-chloro-6-nitrophenol is prepared by chlorination of orthonitrophenol.

* * * * *